(12) United States Patent
Riedhauser et al.

(10) Patent No.: US 9,376,365 B2
(45) Date of Patent: Jun. 28, 2016

(54) HYDROCARBONYLATION OR METHOXYCARBONYLATION OF 1,3-DIENE DERIVATIVES WITH PALLADIUM COMPLEX

(71) Applicant: Firmenich SA, Geneva (CH)

(72) Inventors: Jean-Jacques Riedhauser, Geneva (CH); Oliver Knopff, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/647,307

(22) PCT Filed: Nov. 6, 2013

(86) PCT No.: PCT/EP2013/073171
§ 371 (c)(1),
(2) Date: May 26, 2015

(87) PCT Pub. No.: WO2014/079691
PCT Pub. Date: May 30, 2014

(65) Prior Publication Data
US 2015/0299085 A1    Oct. 22, 2015

(30) Foreign Application Priority Data
Nov. 23, 2012  (EP) ..................................... 12194036

(51) Int. Cl.
*C07C 51/14* (2006.01)
*C07C 67/38* (2006.01)

(52) U.S. Cl.
CPC ................. *C07C 51/14* (2013.01); *C07C 67/38* (2013.01)

(58) Field of Classification Search
CPC ................................. C07C 51/14; C07C 67/38
See application file for complete search history.

(56) References Cited

U.S. PATENT DOCUMENTS

| 4,503,240 A | 3/1985 | Staiger et al. |
| 5,041,642 A | 8/1991 | Jenck |
| 5,350,876 A * | 9/1994 | Drent ...................... C07C 67/38 560/207 |

FOREIGN PATENT DOCUMENTS

| EP | 728732 | 5/2000 |
| WO | WO9206053 | 4/1992 |

OTHER PUBLICATIONS

International Search Report and Written Opinion, application PCT/EP2013/073171, mailed Feb. 19, 2014.
Hosaka et al., Tetrahedron, vol. 27, 1971, 3821-3829.
Tsuji et al., Tetrahedron, vol. 28, 1972, 3721-3725.
van Leeuwen et al., Chem. Re., 2000, 100, 2741-2769.
Xiao et al., J. Org, Chem. 2000, 65, 13, 4138-4144.

* cited by examiner

*Primary Examiner* — Paul A Zucker
(74) *Attorney, Agent, or Firm* — Winston & Strawn LLP

(57) ABSTRACT

The present invention concerns a process of carbonylation of poly-unsaturated diene with high selectivity for the preparation of a β,γ-unsaturated carboxylic acid or ester in the presence of water or alcohol and catalyzed by [PdCl$_2$P$_2$] complex wherein P$_2$ is two mono or one bidentate phosphine ligand.

12 Claims, No Drawings

US 9,376,365 B2

HYDROCARBONYLATION OR METHOXYCARBONYLATION OF 1,3-DIENE DERIVATIVES WITH PALLADIUM COMPLEX

TECHNICAL FIELD

The present invention relates to the field of organic synthesis and more specifically it concerns a process for the preparation of poly-unsaturated allylic carboxylic derivatives as defined in formula (I) via a carbonylation reaction catalyzed by a palladium complex.

PRIOR ART

Many poly-unsaturated allylic carboxylic derivatives as defined in formula (I) are useful products as such or useful intermediates of the preparation of other important raw materials. The poly-isoprenoid derivatives of formula (I) are of particular interest for the perfumery industry, and in particular 4,8-dimethylnona-3,7-dienoic acid or 4,8,12-trimethyl-trideca-3,7,11-trienoic acid. The latter compound is described as an important intermediate for the preparation of industrially relevant compounds such as Cetalox® (dodecahydro-3a,6,6,9a-tetramethyl-naphtho[2,1-b]furan; origin: Firmenich SA, Geneva, Switzerland).

Poly-isoprenoid compounds of formula (I) have been prepared in the literature by many different manners (e.g as carbonylation of allylic intermediate catalyzed by a metal in WO 92/06063, or by hydrolysis of cyano derivatives in U.S. Pat. No. 4,503,240). All these prior art methods are complex or long synthesis and of challenging feasible on an industrial scale. Said compounds (I) have never been reported or suggested in literature as being obtainable by carboxylation of the corresponding diene, raising thus a prejudice to the person skilled in art toward such approach. This is probably because the substrate of formula (II) is very sensitive and chemically unstable and that the carbonylation require harsh conditions including high temperatures and often acidic conditions (as for example described for isoprene or butadiene.

Therefore there is still a need for a method to prepare the target compounds and which allows obtaining said compounds with good yields as well as high regio- and stereo selectivity.

Carbonylation of the simplest and less sensitive isoprene or butadiene have been described in the literature in different ways:
- EP 0728732 described the carbonylation of a diene catalyzed by Pd(AcO)$_2$ in the presence of a monophosphine and a carboxylic acid;
- U.S. Pat. No. 5,041,642 described the carbonylation of a diene catalyzed by Pd complex in the presence of a halogenated hydracid and quaternary onium salt;
- Carbonylation of isoprene in presence of PdCl$_2$ is described in *Tetrahedron* 1971, 3821;
- PdCl$_2$(PPh$_3$)$_2$ is described in J. Tsuji, Y. Mori, M. Hara, *Tetrahedron* 1972, 3721 as catalyst for carbonylation of butadiene.

Substrates described in these examples are simple and do not present any or to minor challenge of selectivity or chemical stability as this is be the case for the substrates of formula (II).

Only thiocarbonylation was reported for this kind of substrate (*Journal of Organic Chemistry* 2000, 65, 4138) in a presence of thiol and a palladium catalyst. However since a thiol is much more acidic than the corresponding alcohol (Bordwell pKa Table), said document is unable to anticipate the reactivity of similar system in the presence of an alcohol. Indeed, as can be seen further below, thiol and alcohol present very different reactivity.

DESCRIPTION OF THE INVENTION

We have now found that the derivatives of formula (I) can be produced in an advantageous manner by means of a new catalytic carbonylation allowing high selectivity and minimal by-products formation.

Therefore, a first object of the present invention is a process for the preparation of a compound of formula (I)

wherein $R^1$ represents a hydrogen atom or a $C_{1-5}$ alkyl group; and

R represents $C_{4-12}$ non conjugated alkenyl or $C_{6-12}$ non conjugated alkadienyl group; by the carbonylation of the corresponding compound of the formula (II)

wherein R has the same meaning as in formula (I);

said carbonylation being performed in the presence of carbon monoxide, a compound of formula $R^1OH$, $R^1$ having the same meaning as above; and a palladium dichloride complex comprising phosphine ligands of the formula $$[PdCl_2P_2] \qquad (III)$$

wherein $P_2$ is two monophosphine monodentate ligands or one biphosphine bidentate ligand.

As mentioned above, the challenge of the present process consists in obtaining the desired product (I) with a good yields as well as high regio- and stereoselectivity; to indeed on the basis of the prior art one may expect many products from the reaction in various molar ratio. Said different products are exemplified, by way on non limiting listing, in the following scheme for myrcene.

Scheme 1: Products obtained under carbonylation conditions of myrcene

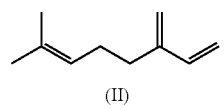
(II)

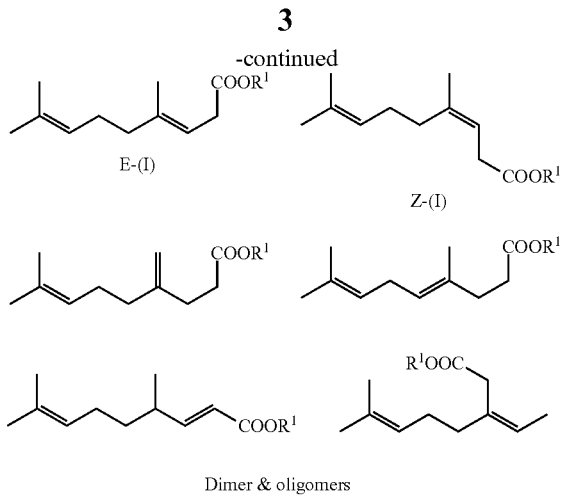

Dimer & oligomers

According to a particular embodiment of the invention, at least 70% of compound (I) are obtained. The compound (I) may have one or two carbon-carbon double bonds which can have different stereochemistry (i.e. can be in a E or Z configuration). Each of said carbon-carbon double bonds of said compounds, independently from each other, can be in a configuration Z or E or a mixture thereof, or in other words each carbon-carbon double bond can be in the form of an essentially pure isomer (i.e. the (3E,7E) one) or in the form of a mixture of isomers, e.g. in the case wherein two carbon-carbon double bonds are present, a mixture comprising the isomers (3E,7E) and (3Z,7E) in various w/w ratio.

According to any one of the above embodiments of the invention, the compound (I) is 4,8,12-trimethyltrideca-3,7,11-trienoic acid or ester, preferably in the form of a mixture of isomers of conformation E and Z wherein the (3E)/(3Z) ratio is comprised between about 1 and 4, or even between about 1 and 2.5.

According to any one of the above embodiments of the invention, the starting compound (II) is β-farnesene, preferably in the form of a mixture of isomers of conformation E and Z wherein the E isomer represents at least 50% w/w, or even 80%, w/w relative to the total weight of the starting material.

According to a particular embodiment of the invention, said $R^1$ represents a $C_{1-3}$ linear or branched alkyl group.

According to any one of the above embodiments of the invention, said R is a group of formula

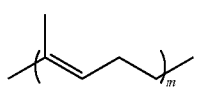

wherein m is 1 or 2.

According to any one of the above embodiments of the invention, the compound of formula (I) is 4,8-dimethylnona-3,7-dienoic acid or ester and the corresponding compound (II) is myrcene, or the compound of formula (I) is 4,8,12-trimethyltrideca-3,7,11-trienoic acid and the corresponding compound (II) is β-farnesene.

The compounds of formula (II) are known compound and are commercially available.

The invention's process has the advantage of being carried out in the absence of acids or bases, to the opposite of some similar processes in the prior art.

The invention's process is carried out in the presence of a catalyst of the formula (III) as above defined.

According to any one of the above embodiments of the invention, said $P_2$ represents two monodentate monophosphines of formula $P(R^2)_2Ar$ wherein $R^2$ represents, simultaneously or independently, a $C_3$-$C_6$ cyclic or branched alkyl group or an Ar group and Ar represents a $C_4$ to $C_{10}$ heteroaromatic or aromatic group optionally substituted by one to five halogen atoms, $C_{1-3}$ halo- or perhalo-hydrocarbon groups, $C_{1-4}$ alkoxy groups or $C_{1-4}$ alkyl groups.

According to a particular embodiment of the invention, said $P_2$ represents two monodentate monophosphines of formula $P(R^2)_2Ar$ wherein $R^2$ represents, simultaneously or independently, a $C_3$-$C_6$ cyclic or branched alkyl group or an Ar group and Ar represents a $C_6$ to $C_{10}$ aromatic group optionally substituted by one to three halogen atoms, $C_{1-3}$ halo- or perhalo-hydrocarbon groups or $C_{1-4}$ alkyl groups.

The expression "halo- or perhalo-hydrocarbon" has here the usual meaning in the art, e.g. groups such as $CF_3$ or $CClH_2$ for instance.

According to any one of the above embodiments of the invention, said $P(R^2)_2Ar$ is a compound wherein $R_2$ represents a $C_{3-4}$ alkyl group branched in the α position, a $C_{5-6}$ cyclic alkyl group or an Ar group and Ar represents a phenyl group optionally substituted by one to two methyl groups, one to two methoxy groups, one to five fluoro atoms, or trifluoromethyl groups or Ar represents a furyl, a benzofuryl or a thienyl group optionally substituted by one to two methyl groups.

According to a particular embodiment of the invention, said $P(R^2)_2Ar$ is a compound wherein $R_2$ represents a $C_{3-4}$ alkyl group branched in the α position, a $C_{5-6}$ cyclic alkyl group or an Ar group and Ar represents a phenyl group optionally substituted by one to two methyl groups or trifluoromethyl groups.

Alternatively, said $P(R^2)_2Ar$ is a compound wherein $R_2$ represents an Ar group and Ar represents a furyl group optionally substituted by one to two methyl groups.

According to any one of the above embodiments of the invention, specific and non limiting examples of such $P(R^2)_2Ar$ are triphenylphosphine, tri-ortho-tolylphosphine, tri-meta-tolylphosphine, tri-para-tolylphosphine, ((4-trifluoromethyl)phenyl)di-tert-butylphosphine, tri-2-furylphosphine.

According to any one of the above embodiments of the invention, said $P_2$ is a bidentate biphosphine having a natural bite-angle comprised between 95° to 130° and more preferably comprised between 98° to 115°. By the expression "natural bite-angle" it is understood the usual meaning in the art, e.g. as defined in P. W. N. M. van Leeuwen, P. C. J. Kamer, J. N. H. Reek, P. Dierkes, Chem. Rev. 2000, 2741.

According to said embodiment, the biphosphine bidentate can be a bidentate bis(di-Ar-phosphine), Ar having the same meaning as above.

Moreover, said $P_2$ bidentate bis(di-Ar-phosphine) can be a compound of formula $(Ar)_2PQP(Ar)_2$ wherein Ar have the same meaning as defined above and Q is oxybis(2,1-phenylene) or 9,9-dimethyl-9H-xanthene-4,5-diyl.

According to any one of the above embodiments of the invention, specific and non limiting examples of such $(Ar)_2PQP(Ar)_2$ is 1,1'-[oxydi-2,1-phenylene)]bis[1,1-diphenylphosphine, 4,5-Bis(diphenylphosphino)-9,9-dimethylxanthene.

The process according to the invention is carried out in the presence of $R^1OH$. According to any one of the above embodiments of the invention, said $R^1$ represents a $C_{1-3}$ alkyl group.

As non-limiting examples of suitable $R^1OH$ one may cite compounds such as water, methanol, ethanol or propanol or iso-propanol.

According to any one of the above embodiments of the invention, the preferred $R^1OH$ is water or methanol.

$R^1OH$ can be added into the reaction medium of the invention's process in a large range of concentrations. As non-limiting examples, one can cite as $R^1OH$ concentration values those ranging from about 0.9 molar equivalents to about 2.5 molar equivalents, relative to the amount of the substrate. Preferably, the $R^1OH$ concentration will be comprised between 0.95 molar equivalents to 1.2 molar equivalents. It goes without saying that the optimum concentration of $R^1OH$ will depend, as the person skilled in the art knows, on the nature of the latter, on the nature of the substrate, of the temperature and on the catalyst used during the process, as well as the desired time of reaction.

The catalyst can be added into the reaction medium of the invention's process in a large range of concentrations. As non-limiting examples, one can cite as complex concentration values those ranging from about 0.1 molar % equivalent to about 10 molar % equivalent, relative to the amount of substrate. Preferably, the complex concentration will be comprised between 0.5 molar % equivalent to 5 molar % equivalent. It goes without saying that the optimum concentration of complex will depend, as the person skilled in the art knows, on the nature of the latter, on the nature of the substrate, of the temperature and on the pressure of CO used during the process, as well as the desired time of reaction.

Free phosphine, e.g. the one corresponding to the phosphine on the catalyst, can be added to the reaction medium of the invention's process in a large range of concentrations. As non-limiting examples, one can cite as phosphine concentration values those ranging from about 0.1 molar equivalent to about 1 molar equivalent, relative to the amount of the catalyst. It goes without saying that the optimum concentration of free phosphine will depend, as the person skilled in the art knows, on the nature of the latter, on the nature of the substrate, of the temperature and on the catalyst used during the process, as well as the desired time of reaction.

The reaction can be carried out in the presence or absence of a solvent. When a solvent is required or used for practical reasons, then any solvent current in such reaction type can be used for the purposes of the invention. Non-limiting examples include THF, Me-THF, MTBE, DME, $Et_2O$, toluene, ethyl acetate. The choice of the solvent is a function of the nature of the substrate and of the complex and the person skilled in the art is well able to select the solvent most convenient in each case to optimize the reaction.

The temperature at which the carbonylation can be carried out is comprised between 0° C. and 160° C., more preferably in the range of between 60° C. and 110° C. Of course, a person skilled in the art is also able to select the preferred temperature as a function of the melting and boiling point of the starting and final products as well as the desired time of reaction or conversion.

In the carbonylation process of the invention, the reaction can be carried out at a CO pressure comprised between 10 bar and 100 bar, more preferably in the range of between 20 bar and 80 bar, and more preferably in the range of between 40 bar and 80 bar. Of course, a person skilled in the art is well able to adjust the pressure as a function of the catalyst load and of the dilution of the substrate in the solvent.

EXAMPLES

The invention, in all its embodiments, will now be described in further detail by way of the following examples, wherein the abbreviations have the usual meaning in the art, the temperatures are indicated in degrees centigrade (° C.). The following abbreviations used herein below have the following meaning:
DPEphos: 1,1'-[(oxydi-2,1-phenylene)]bis[1,1-diphenylphosphine
Xantphos: 4,5-Bis(diphenylphosphino)-9,9-dimethylxanthene.

Reaction scheme: for the compound wherein R is 4,8-dimethyl-3,7-nonadienyl

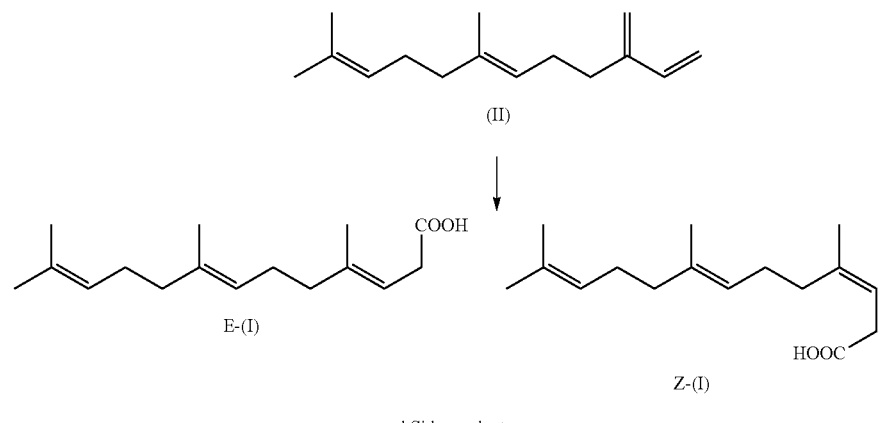

and Side products

The major isomer formed is the E isomer (compound (I)).

Example 1

Catalytic Hydrocarbonylation of β-Farnesene Using Various [PdCl$_2$P$_2$] Complex A Typical Experimental Procedure is as Follows In a 75 mL Keim autoclave, containing a stirring bar, is placed (E)-7,11-dimethyl-3-methylenedodeca-1,6,10-triene (1.02 g, 4.99 mmol) in THF (20 ml). Water (0.088 ml, 4.89 mmol) and 0.11 mmole of [PdCl$_2$P$_2$] (see Table 1) were added. The reactor was sealed and the mixture purged with 3×10 bar of carbon monoxide (CO). While stirring, the autoclave was pressurized to 63 bar with CO and then heated in an oil bath at 90° C.

Once the temperature equilibrated to the set point, the autoclave was pressurized to 68 bar with CO and the reaction allowed to proceed under these conditions. Then the reaction mixture was concentrated on a rotary evaporator to give a crude residue, which was subsequently passed over a chromatography column (SiO$_2$, Et$_2$O/Pentane, 1:4) afforded 3Z,7E-homofarnesic acid and (3E,7E)-homofarnesic acid and further isomeric acids.

The desired product (I) obtained had the same spectral characterization as the ones described in the literature for the same product.

Under these conditions several complex were tested, as reported in Table 1.

TABLE 1

Hydrocarbonylation of β-farnesene using various [PdCl$_2$P$_2$] complexes

| | P$_2$[a] | Bite-angle | Time[b] | Conv.[c] | Yield[d] | Yield based on Conv.[e] | Ratio (3E,7E)/(3Z,7E) |
|---|---|---|---|---|---|---|---|
| 1 | PPh$_3$ | | 20 | 50 | 42 | 84 | 2 |
| 2 | P(o-toluyl)$_3$ | | 20 | 50 | 36 | 72 | 2 |
| 3 | P(t-Bu)$_2$(4-CF$_3$Ph) | | 20 | 50 | 45 | 90 | 2 |
| 4 | DPEphos | 102° | 20 | 40 | 38.4 | 96 | 1.2 |
| 5 | Xantphos[f] | 111° | 108 | 90 | 68 | 76 | 1.3 |

[a] in the case P$_2$ represents monodentate monphosphine, then the two monophosphines are the same compound
[b] in hours
[c] conversion of the starting material in percentage
[d] isolated yield in percentage, calculated over the total amount of starting material engaged
[e] isolated yield in percentage, calculated over the amount of starting material converted
[f] in such a case it was used 0.16 mmole of [PdCl$_2$P$_2$]

Example 2

Catalytic Methoxycarbonylation of β-Farnesene Using [PdCl$_2$(PPh$_3$)$_2$] Complex In a 75 mL Keim autoclave, containing a stirring bar, were placed (E)-7,11-dimethyl-3-methylenedodeca-1,6,10-triene (1.00 g, 4.89 mmol) in THF (20 ml). Methanol (200 μl, 4.94 mmol) and PdCl$_2$(PPh$_3$)$_2$ (80 mg, 0.114 mmol) were added. Then the reactor was sealed and the mixture purged with 3×10 bar of carbon monoxide (CO). While stirring, the autoclave was pressurized to 40 bar with CO and then heated in an oil bath at 90° C. Once the temperature equilibrated to the set point, the autoclave was pressurized to 67 bar with CO and the reaction allowed to proceed under these conditions for 64 h. Then the reaction mixture was concentrated on a rotary evaporator to give a crude residue which was subsequently distilled on a Kugelrohr apparatus (0.3 mbar/170° C.) to afford a colorless liquid (1.17 g) containing (3E,7E)-homofarnesic acid methyl ester and (3Z,7E)-homofarnesic acid methyl ester (61%, 2/1).

The desired product (I) obtained had the same spectral characterization as the ones described in the literature for the same product.

Example 3

Catalytic Methoxycarbonylation of β-Farnesene Using [PdCl$_2$(Tri-2-Furylphosphine)$_2$] Complex In a 300 ml/500 bar reactor Premex were placed (E)-7,11-dimethyl-3-methylenedodeca-1,6,10-triene (10.0 g, 48.9 mmol) in THF (100 ml). Methanol (2.0 ml, 49.4 mmol), and Pd(Cl)$_2$(tri-2-furylphosphine)$_2$ (157 mg, 0.245 mmol; 0.5 mol %) were added. Then the reactor was sealed and the mixture purged with 3×10 bar of carbon monoxide. While stirring, the autoclave was pressurized to 50 bar with CO and the content heated to 90° C. Once the temperature equilibrated to the set point, the autoclave was pressurized to 70 bar with CO and these conditions were then maintained for 68 h. The crude mixture was concentrated on a rotary evaporator affording 11.7 g of yellow liquid. The crude material was bulb to bulb distilled (0.4 mbar, 170° C.) to give 11.3 g of colorless liquid fraction containing (3E,7E)-methyl-4,8,12-trimethyltrideca-3,7,11-trienoate and (3Z,7E)-methyl-4,8,12-trimethyltrideca-3,7,11-trienoate (87%, 2/1).

The desired product (I) obtained had the same spectral characterization as the ones described in the literature for the same product.

Example 4 (Comparative)

Catalytic Thiocarbonylation or Methoxycarbonylation of Myrcene Using Different Catalyst A Typical Experimental Procedure for Thiocarbonylation is as Follows A 75 ml Keim autoclave equipped with a glass liner, was charged with 7-methyl-3-methyleneocta-1,6-diene (see Table2), solvent (see Table2), benzenethiol (see Table2), phosphine (see Table2) and catalyst (see Table2). The reactor was sealed and purged with 3×10 bar of carbon monoxide. While stirring, the autoclave was pressurized with CO and heated up to desired temperature in an oil bath. After 30 min, the pressure was to equilibrated at the desired pressure and the reaction kept under these conditions for 60 h. The crude reaction mixture was then concentrated on the rotary evaporator and the residue passed over a chromatography column (silica gel; pentane/EtOAc 95/5).

A Typical Experimental Procedure for Methoxycarbonylation is as Follows

A 75 ml Keim autoclave was charged with 7-methyl-3-methyleneocta-1,6-diene (see Table2), solvent (see Table2), methanol (see Table2), phosphine (see Table2) and catalyst (see Table2). The reactor was sealed and purged with 3×10 bar of carbon monoxide. While stirring, the autoclave was pressurized with CO and heated up to desired temperature in an oil bath. After 30 min the pressure was equilibrated at the desired pressure. Then the reaction was kept under these conditions for 60 h. The crude reaction mixture was then concentrated on the rotary evaporator and the residue was distillated (0.9 mbar/170° C.) afforded a colorless liquid.

TABLE 2

Thiocarbonylation methoxycarbonylation of myrcene using various catalyst

| | Cat (mmol) | Phosphine (mmol) | RXH (mmol) | Solvent | CO (bar) | T (° C.) | Yield based on Conv. | Ratio E/Z |
|---|---|---|---|---|---|---|---|---|
| Prior Art[a] | [Pd(OAc)$_2$] 0.1 | PPh$_3$ 0.4 | PhSH 2 | CH$_2$Cl$_2$ | 28 | 110 | 31.3 | 1.74 |
| Prior Art[a] | [Pd(OAc)$_2$] 0.1 | PPh$_3$ 0.4 | MeOH 2 | CH$_2$Cl$_2$ | 28 | 110 | 10.3 | 1.86 |
| Prior art with preformed catalyst | [Pd(OAc)$_2$(PPh$_3$)$_2$] 0.22 | | PhSH 10.1 | THF | 68 | 90 | traces | <1 |
| Prior art with preformed catalyst | [Pd(OAc)$_2$(PPh$_3$)$_2$] 0.22 | | MeOH 10.1 | THF | 68 | 90 | 0.84 | 1.89 |
| Present | [Pd(Cl)$_2$(PPh$_3$)$_2$] 0.22 | | MeOH 10.1 | THF | 68 | 90 | 59.4 | 2 |

[a]Xiao, W. J.; Vasapollo, G.; Alper, H. *J. Org. Chem.* 2000, 65 (13), 4138-4144.

As can be seen, the present invention allows to get high yield and good selectivity, while the prior art leads to lower yield of product.

What is claimed is:

1. A process for the preparation of a compound of formula (I)

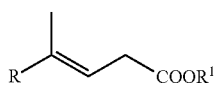

(I)

wherein R$^1$ is a hydrogen atom or a C$_{1-5}$ alkyl group; and R is C$_{4-12}$ non-conjugated alkenyl or C$_{6-12}$ non-conjugated alkadienyl group;
by the carbonylation of the corresponding compound of the formula (II)

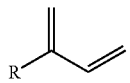

(II)

wherein R has the same meaning as in formula (I);
said carbonylation being performed in the presence of carbon monoxide, a compound of formula R$^1$OH, R$^1$ having the same meaning as above; and a palladium dichloride complex comprising phosphine ligands of the formula [PdCl$_2$P$_2$] (III)
wherein P$_2$ is two monophosphine monodentate ligands or one biphosphine bidentate ligand.

2. A process according to claim 1, wherein R is a group of formula

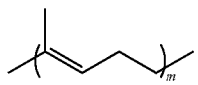

wherein m is 1 or 2.

3. A process according to claim 1, wherein said R$^1$ is a hydrogen or a C$_{1-3}$ alkyl group.

4. A process according to claim 1, wherein said compound (I) is 4,8,12-trimethyltrideca-3,7,11-trienoic acid or ester, in the form of a mixture of isomers of conformation E and wherein the (3E)/(3Z) ratio is between 1 and 2.5.

5. A process according to claim 1, wherein P$_2$ is two monodentate monophosphines of formula P(R$^2$)$_2$Ar wherein R$^2$ is, simultaneously or independently, a C$_{3-}$C$_6$ cyclic or branched alkyl group or an Ar group and Ar is a C$_4$ to C$_{10}$ heteroaromatic or aromatic group optionally substituted by one to five halogen atoms, C$_{1-3}$ halo- or perhalo-hydrocarbon groups, C$_{1-4}$ alkoxy groups or C$_{1-4}$ alkyl groups.

6. A process according to claim 5, wherein P(R$^2$)$_2$Ar represents triphenylphosphine, tri-ortho-tolylphosphine, tri-meta-tolylphosphine, tri-para-tolylphosphine, ((4-Trifluoromethyl)phenyl)di-tert-butylphosphine, or tri-2-furylphosphine.

7. A process according to claim 1, wherein P$_2$ is a bidentate biphosphine ligand having a natural bite-angle that is between 95° and 130°.

8. A process according to claim 7, wherein said bidentate biphosphine is a compound of formula (Ar)$_2$PQP(Ar)$_2$ wherein Ar has the same meaning as defined above and Q is oxybis(2,1-phenylene) or 9,9-dimethyl-9H-xanthene-4,5-diyl.

9. A process according to claim 7, wherein said bis(di-Arphosphine) is 1,1'-[(oxydi-2,1-phenylene)]bis[1,1-diphenylphosphine, or 4,5-Bis(diphenylphosphino)-9,9-dimethylxanthene.

10. A process according to claim 1, wherein R$^1$OH is water, methanol, ethanol, propanol or iso-propanol.

11. A process according to claim 2, wherein R$^1$ is a hydrogen or a C$_{1-3}$ alkyl group.

12. A process according to claim 1, wherein P$_2$ is one biphosphine bidentate ligand.

* * * * *